United States Patent
Goodarznia et al.

(10) Patent No.: US 11,807,589 B2
(45) Date of Patent: Nov. 7, 2023

(54) PROCESS, A SYSTEM, AND AN APPARATUS FOR CATALYTIC CONVERSION OF AN OXIDATIVE DEHYDROGENATION PRODUCT TO AN ALCOHOL

(71) Applicant: Nova Chemicals (International) S.A., Fribourg (CH)

(72) Inventors: Shahin Goodarznia, Calgary (CA); Vasily Simanzhenkov, Calgary (CA); Bolaji Olayiwola, Calgary (CA); Yipei Styles, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 190 days.

(21) Appl. No.: 17/419,382

(22) PCT Filed: Dec. 20, 2019

(86) PCT No.: PCT/IB2019/061210
§ 371 (c)(1),
(2) Date: Jun. 29, 2021

(87) PCT Pub. No.: WO2020/141395
PCT Pub. Date: Jul. 9, 2020

(65) Prior Publication Data
US 2022/0144722 A1 May 12, 2022

Related U.S. Application Data

(60) Provisional application No. 62/788,252, filed on Jan. 4, 2019.

(51) Int. Cl.
*C07C 1/24* (2006.01)
*C07C 5/48* (2006.01)
*C07C 29/147* (2006.01)

(52) U.S. Cl.
CPC .............. *C07C 1/24* (2013.01); *C07C 5/48* (2013.01); *C07C 29/147* (2013.01)

(58) Field of Classification Search
CPC .......... C07C 1/22; C07C 11/04; C07C 29/04; C07C 29/149; C07C 29/16; C07C 29/74;
(Continued)

(56) References Cited

U.S. PATENT DOCUMENTS

| 4,851,344 A | 7/1989 | Simon et al. |
| 8,524,954 B2 | 9/2013 | Ditzel et al. |

(Continued)

FOREIGN PATENT DOCUMENTS

| DE | 3705272 A1 | 9/1988 |
| WO | WO2013191713 A1 | 12/2013 |
| WO | WO2015113058 A1 | 7/2015 |

OTHER PUBLICATIONS

PCT International Search Report and Written Opinion in International Appln. No. PCTIB2019/061210, dated Mar. 31, 2020, 8 pages.

*Primary Examiner* — Sharon Pregler
(74) *Attorney, Agent, or Firm* — Fish & Richardson P.C.

(57) ABSTRACT

A process, a system, and an apparatus are provided for converting a lower alkane to an alkene. Oxygen and a lower alkane are provided to an ODH reactor. At least a portion of the lower alkane is converted to an alkene and an ODH stream comprising the alkene, an oxygenate, water, and carbon monoxide is produced. The ODH stream is provided to a water gas shift/hydrogenation (WGS/H) reactor including a WGS/H catalyst. The ODH stream is reacted within the WGS/H reactor and hydrogen and carbon dioxide are generated from the carbon monoxide and water. At least a
(Continued)

portion of the oxygenate and hydrogen are converted to an alcohol. Additionally, the alcohol may be dehydrated to form additional alkene and water.

30 Claims, 2 Drawing Sheets

(58) Field of Classification Search
CPC ......... C07C 31/08; C07C 5/48; C07C 51/215; C07C 53/08; C07C 9/06
See application file for complete search history.

(56) References Cited

U.S. PATENT DOCUMENTS

| | | | |
|---|---|---|---|
| 9,545,619 B2* | 1/2017 | Wang | ..................... B01J 23/755 |
| 11,078,134 B2* | 8/2021 | Mitkidis | ................... C07C 5/48 |
| 2009/0318743 A1 | 12/2009 | Arnold et al. | |
| 2013/0225876 A1 | 8/2013 | Weiner et al. | |
| 2013/0261347 A1* | 10/2013 | Scates | ................... C07C 51/215 |
| | | | 568/885 |
| 2015/0133700 A1 | 5/2015 | Wollrab | |

* cited by examiner

PROCESS, A SYSTEM, AND AN APPARATUS FOR CATALYTIC CONVERSION OF AN OXIDATIVE DEHYDROGENATION PRODUCT TO AN ALCOHOL

CROSS REFERENCE TO RELATED APPLICATIONS

This application is a United States National Phase Filing of International Patent Application No. PCT/IB2019/061210, which claims the benefit of the filing date of U.S. Provisional Application No. 62/788,252, which was filed on Jan. 4, 2019. The contents of International Patent Application No. PCT/IB2019/061210 and U.S. Application No. 62/788,252 are incorporated by reference in their entirety as part of this application.

TECHNICAL FIELD

The present disclosure relates generally to oxidative dehydrogenation (ODH) of a lower alkane into an alkene. In some examples, the present disclosure relates to catalytic conversion of an ODH product to an alcohol.

BACKGROUND ART

Olefins like ethylene, propylene, and butylene, can be basic building blocks for a variety of commercially valuable polymers. Since naturally occurring sources of olefins do not exist in commercial quantities, polymer producers rely on methods for converting the more abundant lower alkanes into olefins. Typically, a polymer producer utilizes steam cracking to produce alkenes from the alkanes. Steam cracking is a highly endothermic process where steam-diluted lower alkanes are subjected very briefly to a high temperature of at least 800° C. which requires a high energy demand. Additionally, steam cracking can cause coke formation which leads to increased maintenance costs.

Oxidative dehydrogenation (ODH) is an alternative to steam cracking that is exothermic, has a lower energy demand, and produces little or no coke. In ODH, a lower alkane is mixed with oxygen in the presence of a catalyst and optionally an inert diluent at low temperatures such as, for example 300° C., to produce the corresponding alkene. In some examples, various other by-products such as, for example, carbon monoxide, carbon dioxide, and an oxygenate may also be produced in the ODH process. The by-products may be subject to further processing prior to being a marketable product or may be disposed of. The additional processing can increase the complexity of a chemical complex and can include a high energy demand.

SUMMARY OF INVENTION

In one aspect, a method for converting a lower alkane to an alkene is provided. More specifically, oxygen and the lower alkane are provided to an oxidative dehydrogenation (ODH) reactor. At least a portion of the lower alkane is converted to the alkene in the ODH reactor. An ODH outlet stream comprising the alkene, an oxygenate, water, and carbon monoxide is produced. At least a portion of the ODH outlet stream is provided to a water gas shift/hydrogenation (WGS/H) reactor including a WGS/H catalyst. Carbon monoxide and water present in the ODH outlet stream reacts, in the presence of the WGS/H catalyst, to form carbon dioxide and hydrogen. At least a portion of the oxygenate present in the ODH outlet stream reacts with the hydrogen formed to form an alcohol. An alcohol outlet stream comprising at least a substantial portion of the alcohol is produced. In another aspect, at least a portion of the alcohol is dehydrated to form an alkene and water. In another aspect, an apparatus for ODH of a lower alkane to an alkene is provided.

More specifically, the apparatus comprises an ODH reactor and a WGS/H reactor. The ODH reactor comprises an ODH inlet and an ODH outlet. The ODH inlet is suitable for transporting an ODH inlet stream comprising the lower alkane and oxygen into the ODH reactor. The ODH outlet is suitable for transporting an ODH outlet stream comprising the alkene, an oxygenate, water, and carbon monoxide. The WGS/H reactor comprises a WGS/H inlet, a WGS/H outlet, and a WGS/H catalyst. The WGS/H inlet is in fluid communication with the ODH outlet to receive the ODH outlet stream. The WGS/H reactor is suitable to generate hydrogen and carbon dioxide from the carbon monoxide and water of the ODH outlet stream. The WGS/H outlet is suitable for transporting an alcohol outlet stream comprising an alcohol.

In another aspect, a system for ODH of a lower alkane to an alkene is provided. More specifically, the system comprises an ODH reactor and a WGS/H reactor. The ODH reactor is configured to receive oxygen and the lower alkane. The ODH reactor is configured to produce an ODH outlet stream comprising an alkene, an oxygenate, and a carbon-based oxide. The WGS/H reactor comprises a catalyst. The WGS/H reactor is configured to receive the ODH outlet stream and to generate hydrogen and carbon dioxide from the carbon monoxide and water of the ODH outlet stream. At least a portion of the oxygenate and hydrogen is converted to an alcohol.

It is understood that the inventions described in this specification are not limited to the examples summarized in this Summary. Various other aspects are described and exemplified herein.

BRIEF DESCRIPTION OF DRAWING

The features and advantages of the examples, and the manner of attaining them, will become more apparent and the examples will be better understood by reference to the following description of examples taken in conjunction with the accompanying drawings, wherein.

DESCRIPTION OF EMBODIMENTS

Figure 1:
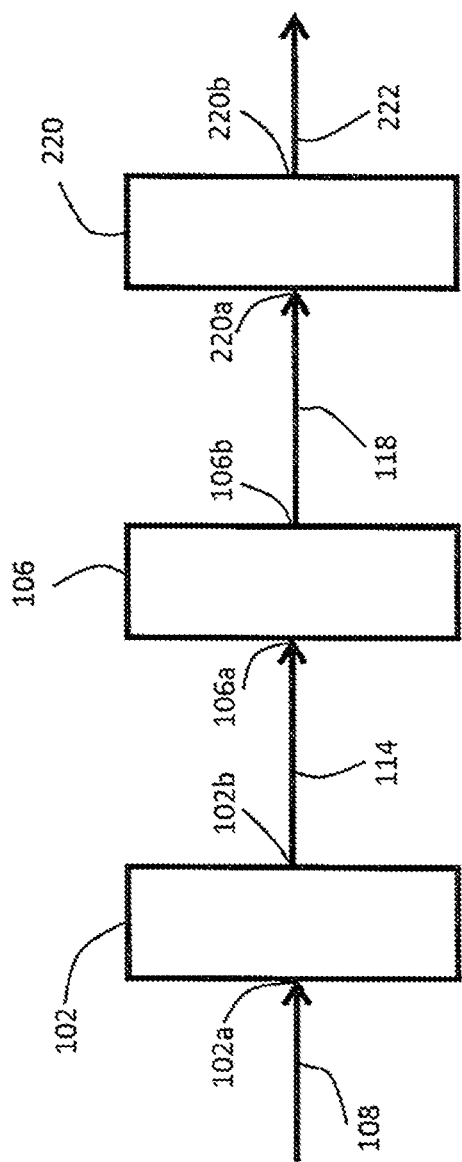
FIG. 1 is a flow diagram illustrating a non-limiting example of a system to convert an alkane to an alkene and including a dehydration reactor.

It is understood that the inventions described in this specification are not limited to the examples summarized in this Summary. Various other aspects are described and exemplified herein.

Certain exemplary aspects of the present disclosure will now be described to provide an overall understanding of the principles of the structure, function, manufacture, and use of the systems and methods disclosed herein. One or more examples of these aspects are illustrated in the accompanying drawings. Those of ordinary skill in the art will understand that the systems, apparatus, and methods specifically described herein and illustrated in the accompanying drawings are non-limiting exemplary aspects and that the scope of the various examples of the present invention is defined by the claims. The features illustrated or described in connection with one exemplary aspect may be combined with the features of other aspects. Such modifications and variations are intended to be included within the scope of the present invention.

Reference throughout the specification to "various examples," "some examples," "one example," or "an example", or the like, means that a particular feature, structure, or characteristic described in connection with the example is included in at least one example. Thus, appearances of the phrases "in various examples," "in some examples," "in one example", or "in an example", or the like, in places throughout the specification are not necessarily all referring to the same example. Furthermore, the particular features, structures, or characteristics may be combined in any suitable manner in one or more examples. Thus, the particular features, structures, or characteristics illustrated or described in connection with one example may be combined, in whole or in part, with the features structures, or characteristics of one or more other examples without limitation. Such modifications and variations are intended to be included within the scope of the present examples.

Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the desired properties, which the present disclosure desires to obtain. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

The grammatical articles "a", "an", and "the", as used herein, are intended to include "at least one" or "one or more", unless otherwise indicated, even if "at least one" or "one or more" is expressly used in certain instances. Thus, the foregoing grammatical articles are used herein to refer to one or more than one (i.e., to "at least one") of the particular identified elements. Further, the use of a singular noun includes the plural, and the use of a plural noun includes the singular, unless the context of the usage requires otherwise.

As used herein, the term "substantial portion" means at least 50 percent by weight. A substantial portion can be 50% to 100% by weight such as, for example, at least 60% by weight, at least 70% by weight, at least 80% by weight, at least 90% by weight, or at least 99% by weight.

As used herein, the term "alkane" refers to an acyclic saturated hydrocarbon. In various examples, an alkane consists of hydrogen and carbon atoms arranged in a linear structure in which all of the carbon-carbon bonds are single bonds. An alkane has the general chemical formula $C_nH_{2n+2}$ and in various examples, for a lower alkane, 'n' is in a range of 2 to 4. In various examples, an alkane refers to one or more of ethane, propane, butane, pentane, hexane, octane, decane and dodecane.

As used herein, the term "alkene" refers to an unsaturated hydrocarbon that contains at least one carbon-carbon double bond. In various examples, alkene refers to alpha olefins. In various examples, alkene refers to one or more of ethylene, propylene, 1-butene, butadiene, pentene, pentadiaene hexene, octene, decene, and dodecene.

As used herein, the terms "alpha olefin" or "α-olefin" refer to a family of organic compounds which are an alkene (also known as olefin) with a chemical formula $C_xH_{2x}$, distinguished by having a double bond at the primary or alpha (a) position. In various examples, alpha olefin refers to one or more of ethylene, propylene, 1-butene, 1-pentene, 1-hexene, 1-octene, 1-decene, and 1-dodecene.

As used herein, the term "substantially free of hydrogen" means that the amount of hydrogen present, if any, is less than 1% by weight of the process stream and may be in amounts such as, for example, less than 0.1%, less than 0.01%, or less than 0.001%.

As used herein, the term "fixed bed reactor" refers to one or more reactors, in series or parallel, often including a cylindrical tube filled with catalyst pellets with reactants flowing through the bed and being converted into products. The catalyst in the reactor may have multiple configurations including, for example, one large bed, several horizontal beds, several parallel packed tubes, multiple beds in their own shells, and/or combinations thereof.

As used herein, the term "fluidized bed reactor" refers to one or more reactors, in series or parallel, often including a fluid (e.g., gas or liquid) which can be passed through a solid granular catalyst, which can be shaped as tiny spheres, at a velocity high enough to suspend the solid granular catalyst and cause the solid granular catalyst to behave like a fluid.

As used herein, the term "HDPE" refers to high density polyethylene, which generally has a density of greater or equal to 0.941 $g/cm^3$. HDPE has a low degree of branching. HDPE can be often produced using chromium/silica catalysts, Ziegler-Natta catalysts or metallocene catalysts.

As used herein, the term "LDPE" refers to low density polyethylene, which can be a polyethylene with a high degree of branching with long chains. Often, the density of a LDPE will range from 0.910-0.940 $g/cm^3$. LDPE can be created by free radical polymerization.

As used herein, the term "LLDPE" refers to linear low density polyethylene, which can be a polyethylene that can have significant numbers of short branches resulting from copolymerization of ethylene with at least one α-olefin comonomer. In some examples, LLDPE has a density in the range of 0.915-0.925 $g/cm^3$. In many examples, the LLDPE can be an ethylene hexene copolymer, ethylene octene copolymer, or ethylene butene copolymer. The amount of comonomer incorporated can be from 0.5 mole % to 12 mole % relative to ethylene, in some examples from 1.5 mole % to 10 mole %, and in other examples from 2 mole % to 8 mole %.

As used herein, the term "MDPE" refers to medium density polyethylene, which can be a polyethylene with some short and/or long chain branching and a density in the range of 0.926-0.940 g/cm³. MDPE can be produced using chromium/silica catalysts, Ziegler-Natta catalysts or metallocene catalysts.

As used herein, the term "VLDPE" refers to very low density polyethylene, which can be a polyethylene with high levels of short chain branching with a typical density in the range of 0.880-0.915 g/cm³. In many examples, VLDPE can be a substantially linear polymer. VLDPE can be typically produced by copolymerization of ethylene with α-olefins. VLDPE can be often produced using metallocene catalysts.

As used herein, the term "gas phase polyethylene process" refers to a process where a mixture of ethylene, optional α-olefin comonomers, and hydrogen can be passed over a catalyst in a fixed or fluidized bed reactor. The ethylene and optional alpha olefins polymerize to form grains of polyethylene, suspended in the flowing gas, which can pass out of the reactor. In various examples, two or more of the individual reactors are placed in parallel or in series, each of which are under slightly different conditions, so that the properties of different polyethylenes from the reactors are present in the resulting polyethylene blend. In many examples, the catalyst system includes, for example, chromium catalysts, Ziegler-Natta catalysts, zirconocene catalysts, and metallocene catalysts and combinations thereof.

As used herein, the term "high pressure polyethylene process" refers to converting ethylene gas into a white solid by heating it at very high pressures in the presence of minute quantities of oxygen (less than 10 ppm oxygen) at 1000 bar-3000 bar and at 80° C.-300° C. In many examples, the high pressure polyethylene process produces LDPE.

As used herein, the term "low pressure polyethylene process" refers to polymerizing ethylene using a catalyst that in many examples includes aluminum at generally lower pressures than the high pressure polyethylene process. In many examples, the low pressure polyethylene process can be carried out at 10 bar-80 bar and at 70° C.-300° C. In various examples, the low pressure polyethylene process provides HDPE. In various examples, an α-olefin comonomer can be included in the low pressure polyethylene process to provide LLDPE.

As used herein, the term "solution polyethylene process" refers to processes that polymerize ethylene and one or more optional α-olefins in a mixture of lower alkane hydrocarbons in the presence of one or more catalysts. In various examples, two or more of the individual reactors can be placed in parallel or in series, each of which can be under slightly different conditions, so that the properties of different polyethylenes from the reactors are present in the resulting polyethylene blend. In many examples the catalysts include, but are not limited to, chromium catalysts, Ziegler-Natta catalysts, zirconocene catalysts, hafnocene catalysts, phosphinimine catalysts, metallocene catalysts, and combinations thereof.

As used herein, the term "slurry polyethylene process" refers to single-tube loop reactors, double-tube loop reactors or autoclaves (stirred-tank reactors) used to polymerize ethylene and optional α-olefins in the presence of a catalyst system and a diluent. Non-limiting examples of diluents include isobutane, n-hexane, or n-heptane. In many examples, two or more of the individual reactors are placed in parallel or in series, each of which can be under slightly different conditions, so that the properties of different polyethylenes from the reactors are present in the resulting polyethylene blend. In many examples, the catalyst system includes, for example, chromium catalysts, Ziegler-Natta catalysts, zirconocene catalysts, hafnocene catalysts, phosphinimine catalysts, metallocene catalysts, and combinations thereof.

As used herein, the term "long chain branching" refers to a situation where during α-olefin polymerization, a vinyl terminated polymer chain can be incorporated into a growing polymer chain. Long branches often have a length that can be longer than the average critical entanglement distance of a linear (e.g., no long chain branching) polymer chain. In many examples, long chain branching effects melt rheological behavior.

As used herein, the term "short chain branching" refers to a copolymer of ethylene with an α-olefin or with branches of less than 40 carbon atoms. In many examples, the α-olefin or branches are present at less than 20% by weight of the polyethylene, in some examples less than 15% by weight. In many examples, the presence of short chain branches can interfere with the formation of the polyethylene crystal structure and can be observed as a lower density compared with a linear (no short chain branching) polyethylene of the same molecular weight.

As used herein, the term "monomer" refers to small molecules containing at least one double bond that can react in the presence of a free radical polymerization initiator to become chemically bonded to other monomers to form a polymer.

As used herein, the term, "olefinic monomer" includes, without limitation, α-olefins, and in many examples, ethylene, propylene, 1-butene, 1-hexene, 1-octene, and combinations thereof.

As used herein, the term "polyolefin" refers to a material, which is prepared by polymerizing a monomer composition containing at least one olefinic monomer.

As used herein, the term "polyethylene" can include, for example, a homopolymer of ethylene, a copolymer of ethylene, and an α-olefin.

As used herein, the term "polypropylene" can include a homopolymer of propylene such as, for example, isotactic polypropylene and syndiotactic polypropylene, a copolymer of propylene, and an α-olefin.

As used herein, the term "polymer" refers to macromolecules composed of repeating structural units connected by covalent chemical bonds and can include, for example, a homopolymer, a random copolymer, a block copolymer, and a graft copolymer.

As used herein, the term "thermoplastic" refers to a class of polymers that can soften or become liquid when heated and can harden when cooled. In many examples, a thermoplastic can be a high-molecular-weight polymer that can be repeatedly heated and remolded. In various examples, a thermoplastic resin can include a polyolefin and an elastomer that has thermoplastic properties.

As used herein, the terms "thermoplastic elastomers" and "TPE" refer to a class of copolymers or a blend of polymers (in many examples a blend of a thermoplastic and a rubber) which includes materials having both thermoplastic and elastomeric properties.

As used herein, the terms "thermoplastic olefin" or "TPO" refer to polymer/filler blends that contain some fraction of polyethylene, polypropylene, block copolymers of polypropylene, rubber, and a reinforcing filler. The fillers can include, for example, talc, fiberglass, carbon fiber, wollastonite, metal oxy sulfate, and combinations thereof. The rubber can include, for example, ethylene-propylene rubber, EPDM (ethylene-propylene-diene rubber), ethylene-butadiene copolymer, styrene-ethylene-butadiene-styrene block copolymers, styrene-butadiene copolymers, ethylene-vinyl acetate copolymers, ethylene-alkyl (meth)acrylate copolymers, and VLDPE such as those available under the FLEXOMER resin trade name from the Dow Chemical Co., Midland, Mich., styrene-ethylene-ethylene-propylene-styrene (SEEPS). These can also be used as the materials to be modified by the interpolymer to tailor their rheological properties.

Unless otherwise specified, all molecular weight values are determined using gel permeation chromatography (GPC). Molecular weights are expressed as polyethylene equivalents with a relative standard deviation of 2.9% for the number average molecular weight ("Mn") and 5.0% for the weight average molecular weight ("Mw"). Unless otherwise indicated, the molecular weight values indicated herein are weight average molecular weights (Mw).

Oxidative dehydration (ODH) couples the endothermic dehydration of an alkane with the strongly exothermic oxidation of hydrogen. For example, ODH of an alkane can comprise contacting an alkane and oxygen in an ODH reactor with an ODH catalyst under reaction conditions (e.g., temperature, pressure, flow rate, etc.) that can promote oxidation of the alkane into the corresponding alkene. The corresponding alkene includes hydrocarbons with the same number of carbons as the alkane used, but with the addition of one carbon to carbon double bond. For example, utilizing ODH, ethane can be converted to ethylene, propane can be converted to propylene, and butane can be converted to butylene.

The flow of gases through the reactor may also be described as the linear velocity of the gas stream (m/s), which is defined in the art as the flow rate of the gas stream/cross-sectional surface area of the reactor/void fraction of the catalyst bed. The flow rate generally means the total of the flow rates of all the gases entering the reactor and is measured where the oxygen and alkane first contact the catalyst and at the temperature and pressure at that point. The cross-section of the reactor is also measured at the entrance of the catalyst bed. The void fraction of the catalyst bed is defined as the volume of voids in the catalyst bed/total volume of the catalyst bed. The volume of voids refers to the voids between catalyst particles and does not include the volume of pores inside the catalyst particles. The linear velocity can range from 5 cm/sec to 1500 cm/sec, for example from 10 cm/sec to 500 cm/sec.

The space-time yield of corresponding alkene (productivity) in g/hour per kg of the catalyst should be not less than 900, for example, greater than 1500, for example, greater than 3000, for example, greater than 3500 at 350 to 400° C. It should be noted that the productivity of the catalyst will increase with increasing temperature until the selectivity is sacrificed.

Any one or more of the ODH catalysts known in the art are suitable for use with the present disclosure. For example, an ODH catalyst containing a mixed metal oxide can be used. When choosing an ODH catalyst a skilled user would appreciate that catalysts can vary with respective to selectivity and activity. Mixed metal oxides are employed as they can provide high selectivity to ethylene without significant loss in activity. Example catalysts are those of the formula:

$$Mo_aV_bNb_cTe_dMe_eO_f$$

wherein: Me is a metal chosen from Ta, Ti, W, Hf, Zr, Sb, Fe, Al and mixtures thereof; a is 1; b is from 0.05 to 1.5; c is from 0 to 3; d is from 0 to 5; e is from 0 to 2; and f is a number to satisfy the valence state of the catalyst. Additional components may also include goethite, boehmite, and hematite.

Additionally, reaction conditions can be controlled to adjust the selectively and yield of the ODH reactor products. As known in the art, conditions will vary and can be optimized for a particular alkane, for a specific ODH catalyst, a select product, and/or a particular inert diluent.

A product of an ODH reaction can be an oxygenate such as, for example, acetic acid, acrylic acid, maleic acid, and maleic anhydride. The oxygenate can require purification and/or further processing in order to generate a marketable product. For example, water may have to be removed from the oxygenate and an additional material such as, for example, hydrogen may have to be added to the oxygenate to facilitate further processing of the oxygenate. The additional material can add complexity to the process and can create a hazardous operational condition. Thus, a method, a system, and an apparatus are provided which can reduce the amount of purification and further processing required for the oxygenate. More specifically, a method, a system, and an apparatus are provided for converting a lower alkane to an alkene. Oxygen and a lower alkane can be provided to an ODH reactor. At least a portion of the lower alkane can be converted to an alkene in the ODH reactor and an ODH outlet stream comprising the alkene, an oxygenate, water, and carbon monoxide can be produced. At least a portion of the ODH outlet stream can be provided to a water gas shift/hydrogenation (WGS/H) reactor including a WGS/H catalyst. The ODH outlet stream can be reacted within the WGS/H reactor and hydrogen and carbon dioxide can be generated from the carbon monoxide and water. At least a portion of the oxygenate and hydrogen are converted to an alcohol. An alcohol outlet stream comprising at least a substantial portion of the alcohol can be produced.

Referring to FIG. 1, illustrated is a flow diagram of a non-limiting example of a system 100 to convert an alkane to an alkene. As illustrated, an ODH reactor 102 and a water gas shift/hydrogenation (WGS/H) reactor 106 can be in operative communication. For example, an ODH outlet 102b of the ODH reactor 102 can be in fluid communication with a water gas shift/hydrogenation (WGS/H) inlet 106a of the WGS/H reactor 106 via ODH outlet line 114.

The ODH reactor 102 can comprise an ODH inlet 102a which can be configured to receive an ODH inlet stream from an ODH inlet line 108 and can be suitable to transport the ODH inlet stream into the ODH reactor 102. The ODH inlet stream can comprise a gaseous mixture of a lower alkane and oxygen. In various examples, the ODH inlet stream additionally can include at least one of carbon dioxide, water (e.g., steam), and an inert diluent. The inert diluent can comprise, for example, nitrogen. The concentration of the oxygen and the lower alkane within the mixture in the ODH inlet stream and the temperature and pressure of the ODH inlet stream can be adjusted such that the mixture can be outside of the flammability limits of the lower alkane.

In various examples, there may be multiple ODH inlet lines configured to provide the ODH inlet stream to the ODH reactor 102. For example, each reactant (e.g., lower alkane, oxygen, water (e.g., steam), carbon dioxide, and inert diluent) may be added directly to the ODH reactor 102, each in separate inlet lines. Alternatively, one or more reactants may be pre-mixed and added in more than one inlet line. In various example, reactants may be mixed together prior to the ODH reactor 102 and subsequently introduced into the ODH reactor in a common ODH inlet line. In various examples, steam may be added indirectly as water mixed with an additional reactant and the resulting mixture can be preheated before entering the ODH reactor 102. When adding steam indirectly as water, the preheating process can increase the temperature of the mixture so that the water can be substantially converted to steam before entering the ODH reactor 102.

The ODH reactor 102 includes an ODH catalyst capable of catalyzing the ODH of the reactants to products such as, for example, an alkene, carbon monoxide, and an oxygenate. The catalyst may be, for example, a mixed metal oxide catalyst. In various examples, the products may additionally include at least one of carbon dioxide and water.

The ODH catalyst composition, temperature and pressure of the ODH reactor 102, and the composition of the ODH inlet stream can be adjusted in order to vary the composition of products as known by one of ordinary skill in the art. For example, the ratio of the lower alkane to oxygen can be outside of the upper flammability limit of the mixture. In various examples, the oxygen concentration in the ODH inlet stream can be in a range of 0.1% to 30% by weight of the ODH inlet stream, and in some examples range from 0.1% to less than 30% by weight, less than 25% by weight, or less than 20% by weight. In various examples, the lower alkane concentration in the ODH inlet stream can range from 0.1% to 50% by weight of the ODH inlet stream, and in some examples range from 0.1% to less than 50% by weight or less than 40% by weight.

In various examples, increasing the steam concentration in the ODH inlet stream can increase the amount of oxygenate produced relative to the alkene produced in the ODH reactor 102. In various examples, reducing the steam concentration in the ODH inlet stream can decrease the amount of oxygenate produced relative to the alkene produced in the ODH reactor 102. The concentration of steam in the ODH inlet stream can be in a range of 0.1% to 40% by weight of the total ODH inlet stream, and in some examples range from 0.1% to less than 40% by weight, or less than 25% by weight. In various examples, the concentration of steam in the ODH inlet stream can be at least 1% by weight. In various examples, the ODH inlet stream can comprise 20% oxygen by weight, 40% lower alkane by weight, and the balance being water (e.g., steam), carbon dioxide, and/or an inert diluent.

In various examples, the ODH process has a selectivity for the corresponding alkene (e.g., ethylene in the case of ethane ODH) of greater than 95% such as, for example, greater than 98%. The gas hourly space velocity (GHSV) within the ODH reactor 102 can be from 500 to 30000 $h^{-1}$ and in some examples the GHSV within the ODH reactor 102 can be greater than 1000 $h^{-1}$. In various examples, the space-time yield of corresponding alkene (e.g., productivity) in grams (g)/hour per kilogram (kg) of the catalyst can be at least 900 such as, for example, at least 1500, at least 3000, or at least 3500, at an ODH reactor temperature of 350° C. to 400° C. In various examples, the productivity of the catalyst can increase with increasing temperature in the ODH reactor 102 until the selectivity of the alkene decreases.

Use of an ODH reactor for performing an ODH process consistent with the present disclosure falls within the knowledge of the person skilled in the art. For best results, the oxidative dehydrogenation of a lower alkane may be conducted at temperatures from 300° C. to 450° C., typically, from 300° C. to 425° C., for example, from 330° C. to 400° C., at pressures from 0.5 to 100 psi (3.447 to 689.47 kPag), for example, from 15 to 50 psi (103.4 to 344.73 kPag), and the residence time of the lower alkane in the reactor is typically from 0.002 to 30 seconds, for example, from 1 to 10 seconds.

In some embodiments, the process has a selectivity for the corresponding alkene (ethylene in the case of ethane ODH) of greater than 85%, for example, greater than 90%. The flow of reactants and inert diluent can be described in any number of ways known in the art. Typically, flow is described and measured in relation to the volume of all feed gases (reactants and diluent) that pass over the volume of the active catalyst bed in one hour, or gas hourly space velocity (GHSV). The GHSV can range from 500 to 30000 $h^{-1}$, for example greater than 1000 $h^{-1}$. The flow rate can also be measured as weight hourly space velocity (WHSV), which describes the flow in terms of the weight, as opposed to volume, of the gases that flow over the weight of the active catalyst per hour. In calculating WHSV the weight of the gases may include only the reactants but may also include diluents added to the gas mixture. When including the weight of diluents, when used, the WHSV may range from 0.5 $h^{-1}$ to 50 $h^{-1}$, for example from 1.0 to 25.0 $h^{-1}$.

The products of the ODH reaction can leave the ODH reactor 102 through the ODH outlet 102b in an ODH outlet stream. The ODH outlet 102b can be configured to receive the ODH outlet stream and can be suitable to transport the ODH outlet stream out of the ODH reactor 102 into the ODH outlet line 114. In various examples, in addition to the products, the ODH outlet stream can include unreacted components from the ODH inlet stream such as, for example, lower alkane, carbon monoxide, carbon dioxide, oxygen, water (e.g., steam), inert diluent, and combinations thereof.

Any of the known reactor types applicable for the ODH of an alkane may be used with the present disclosure. For example, a fixed bed reactor, a fluidized bed reactor, or combinations thereof can be used for the ODH reactor 102. In a typical fixed bed reactor, reactants are introduced into the reactor at an inlet and flow past an immobilized catalyst. Products are formed and leave through the outlet of the reactor. A person skilled in the art would know which features are required with respect to shape and dimensions of the reactor, inputs for reactants, outputs for products, temperature and pressure control, and means for immobilizing the catalyst. Shell-and-tube type reactors are well known as being applicable for use in ODH reactors, owing to the exothermic nature of the reaction. These reactors are designed with the goal of efficient removal of heat to prevent runaway reactions.

In a typical fluidized bed reactor, the catalyst bed can be supported by a porous structure or a distributor plate and located near a lower end of the reactor. Reactants flow through the fluidized bed reactor at a velocity sufficient to fluidize the bed (e.g., the catalyst rises and begins to swirl around in a fluidized manner). The reactants can be converted to products upon contact with the fluidized catalyst and the reactants are subsequently removed from an upper end of the reactor. A person of ordinary skill in the art would know which features are required with respect to shape and dimensions of the reactor, the shape and size of the distributor plate, the input temperature, the output temperature, the reactor temperature and pressure, inputs for reactors, outputs for reactants, and velocities to achieve fluidization.

In various examples, there may be multiple ODH reactors connected in series or in parallel. Each ODH reactor may be the same or different. For example, each ODH reactor can contain the same or different ODH catalyst. In various examples, the multiple ODH reactors can each be a fixed bed reactor, can each be a fluidized bed reactor, or can be combinations of fixed bed reactors and fluidized bed reactors.

Regardless of the configuration of the ODH reactor 102, the ODH outlet 102b can be in fluid communication with the WGS/H inlet 106a of the WGS/H reactor 106 via the ODH outlet line 114 to direct the ODH outlet stream to the WGS/H reactor 106. The WGS/H inlet 106a can be configured to receive the ODH outlet stream from the ODH outlet line 114 and can be suitable to transport the ODH outlet stream into the WGS/H reactor 106.

In an alternative configuration the ODH outlet stream can be in fluid communication with a separator, the separator having an inlet configured to receive the ODH outlet stream from the ODH outlet line 114 and can be suitable to transport the ODH outlet stream into the separator. The separator may include cooling and quenching of the ODH outlet stream for the purpose of separating out water and oxygenate from the ODH outlet stream, producing an alkene outlet stream and an oxygenate outlet stream. The separator may also have an alkene outlet configured to remove the alkene outlet stream from the separator and an oxygenate outlet for removing the oxygenate outlet stream from the separator. The oxygenate outlet stream would be provided to the WGS/H reactor 106 through the WGS/H inlet 106a in place of the ODH outlet stream. In various embodiments, an ODH outlet stream and an oxygenate outlet stream can be provided to the WGS/H reactor 106 via WGS/H inlet 106a.

The separator can be a quench tower, an oxygenate scrubber, a flash drum, the like, or combinations thereof. The separator can be configured to remove at least a substantial portion of the alkene from the ODH outlet stream. The separator can produce an alkene outlet stream comprising at least a substantial portion of the alkene from the ODH outlet stream. In various examples, the alkene outlet stream can comprise additional components from the ODH outlet stream such as for example, a portion of the carbon monoxide, a portion of the carbon dioxide, a portion of the oxygen, a portion of the oxygenate, a portion of the inert diluent, a portion of the water (e.g., steam), and a portion of the unreacted alkane.

The separator can produce an oxygenate outlet stream comprising at least a substantial portion of the oxygenate from the ODH outlet stream. In various examples, the oxygenate outlet stream can comprise additional components from the ODH outlet stream such as, for example, a substantial portion of the water, a portion of the carbon monoxide, a portion of the carbon dioxide, and a portion of the oxygen. In various examples, the oxygenate outlet stream comprises a molar ratio of water to oxygenate of greater than 1:1 such as, for example, 1.1:1, or 2:1.

The temperature of the ODH outlet stream, or oxygenate outlet stream when using a separator, can be adjusted prior to entering the WGS/H reactor 106. For example, the temperature of the ODH outlet stream prior to entering the WGS/H reactor 106, or separator, can be at a temperature of at least 40° C. or at least 50° C. such as, for example, 40° C. to 450° C. or 50° C. to 200° C.

The WGS/H reactor 106 can be configured to facilitate a water gas shift (WGS) reaction and a hydrogenation reaction. In various examples, combining both the WGS and hydrogenation reactions into a single reactor can eliminate the need to add hydrogen and the need to remove water from the oxygenate outlet stream prior to hydrogenation. For example, the WGS/H reactor 106 can generate, in situ, hydrogen for hydrogenation of the oxygenate using the WGS reaction. The WGS/H reactor can comprise a WGS/H catalyst to convert a portion of the carbon monoxide and a portion of the water in the oxygenate outlet stream to carbon dioxide and hydrogen as shown in Scheme 1.

 Scheme 1:

As Scheme 1 indicates, carbon monoxide is a reactant. As a result, when using a separator prior to the WGS/H reactor a user may be required to add carbon monoxide to the oxygenate outlet stream as the levels of carbon monoxide may not be sufficient to convert a desirable amount of the water present in the stream. For this reason, one example of a preferred configuration includes providing the ODH outlet stream directly to the WGS/H reactor, without first passing through a separator.

The WGS/H catalyst can comprise a metal oxide catalyst. The metal oxide catalyst can be non-acidic. For example, the non-acidic catalyst may not contain a chemical species that contains an empty orbital which can be capable of accepting an electron. In various examples, the metal oxide catalyst can be a solid catalyst. The metal oxide catalyst can comprise, copper oxide, zinc oxide, aluminum oxide, iron oxide, chromium oxide, magnesium oxide, a noble metal, and ceria. For example, the metal oxide catalyst can comprise at least one of copper, iron, platinum, tin, and chromium. The WGS/H reactor 106 can operate at a temperature in a range of 100° C. to 500° C. such as for example, 200° C. to 300° C. The WGS/H reactor 106 can operate at a pressure in a range of 100 kilopascals (kPag) to 8375 kPag such as, for example, 100 kPag to 500 kPag. In various examples, the liquid hourly space velocity (LHSV) in the WGS/H reactor 106 can be at least 0.1 $h^{-1}$ such as, for example, a range of 0.3 $h^{-1}$ to 0.7 $h^{-1}$, or at least 2 $h^{-1}$.

The WGS/H reactor 106 can contact the hydrogen with the oxygenate and can be configured to perform a hydrogenation reaction. In various examples, the WGS/H catalyst can catalyze the WGS/H reaction and the hydrogenation reaction. For example, the WGS/H catalyst can facilitate conversion of a portion of the hydrogen and a portion of the oxygenate from the oxygenate outlet stream to an alcohol and water. As an example, the hydrogenation of acetic acid is shown in Scheme 2. In various examples, the alcohol can comprise at least one of ethanol, propanol, and butanol.

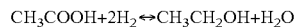
 Scheme 2:

The products of the WGS and hydrogenation reaction can exit the WGS/H reactor 106 through the WGS/H outlet 106b in a WGS/H outlet stream. The WGS/H outlet 106b can be configured to receive the WGS/H outlet stream and can be suitable to transport the WGS/H outlet stream out of the WGS/H reactor 106 into the WGS/H outlet line 118. Moreover, the WGS reaction can be exothermic. Thus, the temperature of the oxygenate outlet stream can be maintained at a temperature of less than 350° C. such that the WGS/H outlet stream does not reach above a select temperature such as, for example 550° C.

Various reactor types applicable for a WGS reaction and/or a hydrogenation reaction can be employed for use with the present disclosure. For example, a fixed bed reactor, a fluidized bed reactor, or combinations thereof can be used for the WGS/H reactor 106. In various examples, there may be multiple WGS/H reactors connected in series or in parallel. In various examples a shell-and-tube reactor design may be appropriate due to the exothermic nature of the WGS/H reaction.

The alcohol can be converted to another product such as, for example, an alkene, an ether, an aldehyde, the like, and combinations thereof. For example, if the alcohol comprises ethanol, the ethanol can be converted to ethylene, diethyl ether, acetaldehyde, the like, and combinations thereof.

Referring to FIG. 1, a flow diagram of a non-limiting example of a system 200 to convert an alkane to an alkene and the system 200 including a dehydration reactor 220 is provided. As illustrated, the WGS/H outlet 106b can be in fluid communication with a dehydration inlet 220a of the dehydration reactor 220 via the WGS/H outlet line 118 to direct the WGS/H outlet stream to the dehydration reactor 220. The dehydration inlet 220a can be configured to receive the WGS/H outlet stream from the WGS/H outlet line 118 and can be suitable to transport the WGS/H outlet stream into the dehydration reactor 220.

The dehydration reactor can convert at least a portion of the alcohol within the WGS/H outlet stream into an alkene. For example, the dehydration of ethanol can be shown in Scheme 3.

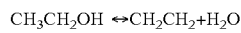  Scheme 3:

The dehydration reactor 220 can produce a dehydration outlet stream comprising the alkene generated within the dehydration reactor 220. The dehydration outlet stream can exit the dehydration reactor 220 through the dehydration outlet 220b. The dehydration outlet 220b can be configured to receive the dehydration outlet stream and can be suitable to transport the dehydration outlet stream out of the dehydration reactor 220 into the dehydration outlet line 222. The dehydration reactor 220 can operate at a temperature of 100° C. to 300° C. such as for example, 175° C. to 275° C., 150° C. to 250° C. and in some examples, the dehydration reactor 220 can operate at a temperature of less than 200° C.

Since the ODH process operates at a temperature of 300° C. to 450° C., the WGS/H reactor 106 can operate at a temperature of 100° C. to 500° C. and the dehydration reactor can operate at a temperature of 100° C. to 300° C., an energy savings can be achieved by combining the processes together. For example, the residual heat in the ODH outlet stream can facilitate the WGS and hydrogenation reactions in the WGS/H reactor 106. In various examples, the residual heat in the WGS/H outlet stream can facilitate the dehydration reaction in the dehydration reactor 220. In various examples, operating the WGS/H reactor 106 in fluid communication with the ODH reactor 102 enables a reduction in energy required to produce the alcohol relative to operating the processes separately.

Concentrations of the components within the system can be measured any at point in the process using any means known in the art. For example, a detector such as a gas chromatograph, an infrared spectrometer, and a Raman spectrometer can be disposed downstream or upstream of ODH reactor 102, separator 104, WGS/H reactor 106, and dehydration reactor 220.

In various examples, the WGS/H outlet stream, the dehydration outlet stream, or both may be directed to a separator such as those described. Separation of oxygenate, water, and alcohol may be promoted so that the alkenes within the streams can be isolated for downstream applications.

In various examples, the ODH inlet stream comprises mixtures that fall within the flammability limits of the components. For example, the mixture may exist in conditions that prevent propagation of an explosive event. In these examples, the flammable mixture can be created within a medium where ignition can be immediately quenched. In various examples, oxygen and the lower alkanes can be mixed at a point where they are surrounded by a flame arresting material. Thus, any ignition can be quenched by the surrounding material. Flame arresting material includes, for example, metallic or ceramic components, such as stainless-steel walls or ceramic supports. In various examples, oxygen and lower alkanes can be mixed at a low temperature, where an ignition event may not lead to an explosion, then the mixture can be introduced into the ODH reactor 102 before increasing the temperature. Therefore, the flammable conditions may not exist until the mixture can be surrounded by the flame arresting material inside of the ODH reactor 102.

In various examples, the olefins produced using an ODH reactor 102, or any of the processes or complexes described herein, can be used to make various olefin derivatives utilizing a polymerization reactor. Olefin derivatives include, but are not limited to polyethylene, polypropylene, ethylene oxide, propylene oxide, polyethylene oxide, polypropylene oxide, vinyl acetate, vinyl chloride, acrylic esters (e.g., methyl methacrylate), thermoplastic elastomers, thermoplastic olefins, blends thereof, and combinations thereof.

In various examples, ethylene and optionally α-olefins can be produced in an ODH reactor 102, or any of the processes or complexes described herein, and are used to make polyethylene utilizing a polymerization reactor. The polyethylene made from the ethylene and optional α-olefins described herein can include homopolymers of ethylene, copolymers of ethylene and α-olefins, resulting in HDPE, MDPE, LDPE, LLDPE and VLDPE.

The polyethylene produced using the ethylene and optional α-olefins described herein can be produced using any suitable polymerization process and equipment. Suitable ethylene polymerization processes include, but are not limited to gas phase polyethylene processes, high pressure polyethylene processes, low pressure polyethylene processes, solution polyethylene processes, slurry polyethylene processes and suitable combinations of the above arranged either in parallel or in series.

A process for converting a lower alkane to an alkene according to the present disclosure can include providing an input stream comprising oxygen and the lower alkane to an ODH reactor 102. At least a portion of the lower alkane can be converted to the alkene in the ODH reactor 102. In various examples, the alkane comprises ethane and the alkene comprises ethylene. In various examples, the alkane comprises propane and the alkene comprises propylene. In various examples, the alkane comprises butane and the alkene comprises butylene. An ODH outlet stream comprising the alkene, an oxygenate, water, and carbon monoxide can be produced. In various examples, the ODH outlet stream additionally includes at least one of an unreacted alkane, carbon dioxide, and oxygen. In various examples, the ODH outlet stream can be substantially free of hydrogen. In various examples, the oxygenate can comprise at least one of acetic acid, acrylic acid, maleic acid, and maleic anhydride.

In various examples, the temperature of the ODH outlet stream can be adjusted by varying reaction conditions in the ODH reactor 102, passing the ODH outlet stream through a heat exchanger, or combinations thereof. In various examples, the ODH outlet stream can have a temperature of 50° C. to 350° C.

The ODH outlet stream can be provided to a WGS/H reactor 106 comprising a WGS/H catalyst. In various examples, the WGS/H catalyst can be non-acidic. In various examples, the WGS/H catalyst can comprise at least one of copper, iron, platinum, tin, and chromium. In various examples, the WGS/H reactor 106 can be maintained at a temperature of 100° C. to 500° C. In various examples, the WGS/H reactor 106 can be maintained at a pressure of 100 kPag to 500 kPag.

The WGS/H reactor 106 can generate hydrogen, in situ, from the carbon monoxide and water of the ODH outlet stream. At least a portion of the oxygenate and hydrogen can be converted to an alcohol. An alcohol outlet stream comprising at least a substantial portion of the alcohol can be produced. In various examples, the alcohol comprises at least one of ethanol, propanol, and butanol.

The alcohol outlet stream can be provided to a dehydration reactor and at least a portion of the alcohol in the alcohol outlet stream can be converted to a second alkene. In various examples, the second alkene is the same species of alkene produced in the ODH reactor and comprises at least one of ethylene, propylene, and butylene. In various examples, the WGS/H reactor and the dehydration reactor may be a single reactor. In this instance, the reactor may include a WGS/H catalyst and a dehydration catalyst, spatially separated so that as components of the ODH outlet stream move through the single reactor contact with the WGS/H catalyst precedes contact with the dehydration catalyst. The heat produced by the reaction with the WGS/H catalyst supports the dehydration catalyst for removing $H_2O$ from the alcohol to produce an alkene.

Olefin derivatives can be produced from the alkenes, including the alkene produced in the ODH reactor and the second alkene produced in the dehydration reactor.

The present disclosure can provide a route to convert an alkane into an alkene, reduction of an undesired product, an opportunity to run at a high alkane conversion (e.g., greater than 95%) where an increase in oxygenate selectivity may result and generate an additional marketable product.

alcohol outlet stream comprising at least a substantial portion of the alcohol.

EXAMPLES

The WGS/H reactor 106 and the dehydration reactor 220 were computationally modeled using ASPEN Plus® version 8.6 chemical process simulation software. The ODH outlet line 114 was in fluid communication with the WGS/H inlet 106a of the WGS/H reactor 106. The WGS/H outlet 106b of the WGS/H reactor 106 was in fluid communication with the dehydration inlet 220a of the dehydration reactor 220 via the WGS/H outlet line 118. The WGS/H reactor 106 and the dehydration reactor 220 were modeled as RGibbs reactors and were assigned the EoS property method of SR-POLAR.

Example 1 to 5

For examples 1 to 5, the composition of the ODH (O) outlet stream was set with a 1 kg/hr mass flow rate and the O outlet stream comprised acetic acid, water, and carbon monoxide as illustrated in Table 1. Five different simulations were performed while varying the temperature of the WGS/H reactor and the temperature of the dehydration reactor from 100° C. to 500° C. in 100° C. increments as illustrated in Table 1. The pressure of the WGS/H reactor and the dehydration reactor were each kept constant at 100 kPag.

TABLE 1

| | | O outlet stream | WGS/H Outlet Stream | | | | | Dehydration Outlet Stream | | | | |
|---|---|---|---|---|---|---|---|---|---|---|---|---|
| | Experiment | Ex. 1-5 | Ex. 1 | Ex. 2 | Ex. 3 | Ex. 4 | Ex. 5 | Ex. 1 | Ex. 2 | Ex. 3 | Ex. 4 | Ex. 5 |
| | Temp (° C.) | 100 | 100 | 200 | 300 | 400 | 500 | 100 | 200 | 300 | 400 | 500 |
| | Volume Flow (L/min) | 19.48 | 17.58 | 28.91 | 41.91 | 49.35 | 56.69 | 19.40 | 28.32 | 39.39 | 49.09 | 56.69 |
| Mass | $CH_3OOH$ | 0.3 | 0.07 | 0.02 | 0 | 0 | 0 | 0.03 | 0 | 0 | 0 | 0 |
| Fraction | $H_2O$ | 0.4 | 0.28 | 0.15 | 0.08 | 0.12 | 0.16 | 0.34 | 0.26 | 0.15 | 0.12 | 0.16 |
| | CO | 0.3 | 0 | 0 | 0.08 | 0.14 | 0.2 | 0 | 0 | 0.03 | 0.14 | 0.2 |
| | $CO_2$ | 0 | 0.48 | 0.7 | 0.79 | 0.69 | 0.6 | 0.49 | 0.63 | 0.73 | 0.69 | 0.6 |
| | $C_2H_5OH$ | 0 | 0.18 | 0.09 | 0 | 0 | 0 | 0.04 | 0 | 0 | 0 | 0 |
| | $H_2$ | 0 | 0.01 | 0.04 | 0.06 | 0.05 | 0.05 | 0.01 | 0.02 | 0.04 | 0.05 | 0.05 |
| | $C_2H_4$ | 0 | 0 | 0 | 0 | 0 | 0 | 0.1 | 0.09 | 0.04 | 0 | 0 |
| | Heat of Reaction (KJ/mol) | 223.29 | 258.02 | 199.26 | 168.79 | 172.10 | 176.63 | 234.68 | 204.53 | 184.72 | 173.04 | 176.64 |

Figure 2:
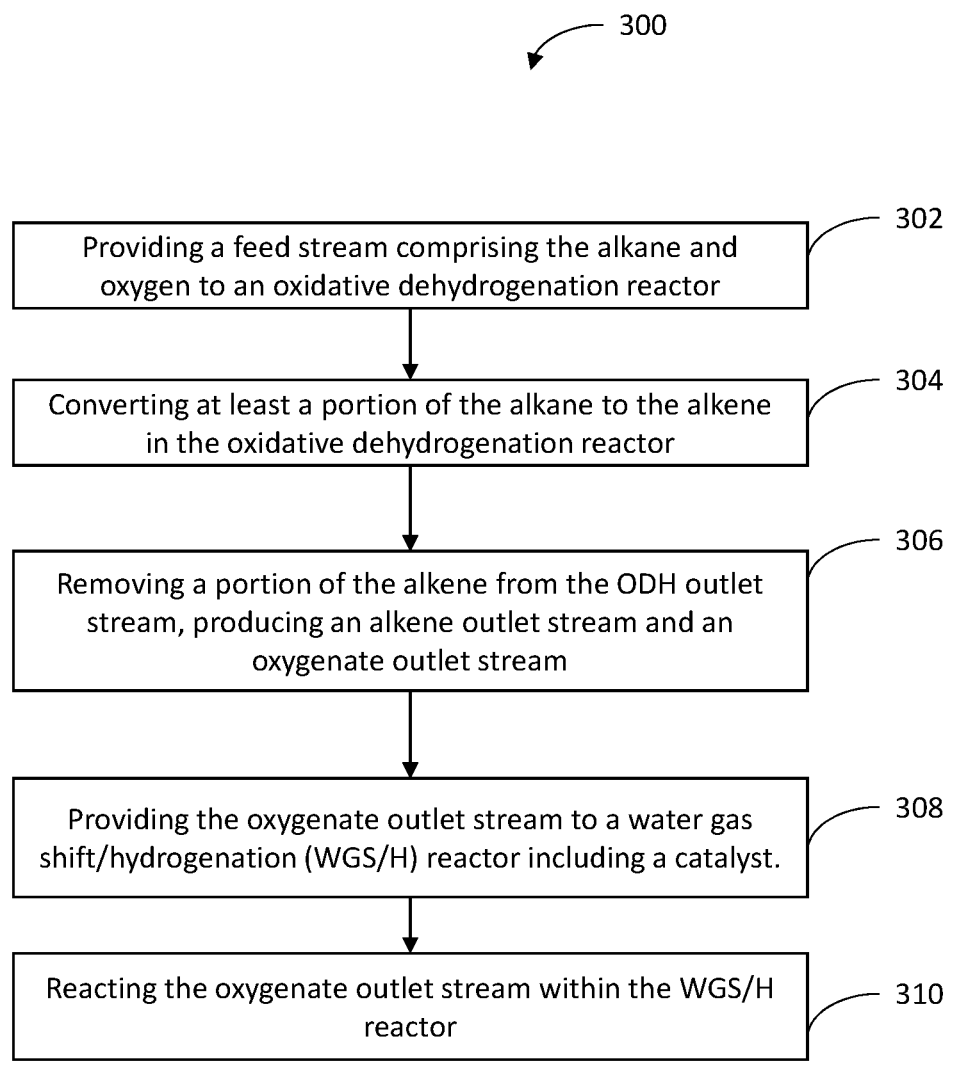
FIG. 2 is a process flow diagram of a method for converting an alkane to an alkene.

FIG. 2 is a process flow diagram of a method 300 for converting a lower alkane to an alkene. The method 300 begins at block 302 with providing an input stream comprising oxygen and the lower alkane to an oxidative dehydrogenation (ODH) reactor.

At block 304 at least a portion of the lower alkane is converted to the alkene in the ODH reactor. The conversion produces an ODH outlet stream comprising the alkene, an oxygenate, water, and carbon monoxide.

At block 306, a substantial portion of the alkene is removed from the ODH outlet stream to produce an alkene outlet stream and an oxygenate outlet stream. The alkene outlet stream includes the substantial portion of the alkene. The oxygenate outlet stream includes a substantial portion of the oxygenate, a substantial portion of the water, and a portion of the carbon monoxide.

At block 308, the oxygenate outlet stream is provided to a water gas shift/hydrogenation (WGS/H) reactor including a catalyst. At block 310, the oxygenate outlet stream is reacted within the WGS/H reactor. The reaction generates hydrogen, in situ, from the carbon monoxide and water of the oxygenate outlet stream, converts a portion of the oxygenate and hydrogen to an alcohol, and produces an As shown in Table 1, the exothermic nature of the WGS reaction and hydrogenation reactions within the WGS/H reactor caused a substantial portion of the acetic acid, carbon monoxide, and water to be converted to ethanol, carbon dioxide, and hydrogen. Additionally, the dehydration reaction of the ethanol to ethylene in the dehydration reactor was favored at temperatures of less than 300° C. and a high conversion of the carbon monoxide in the WGS/H reactor is thermodynamically favored at temperatures less than 300° C. for these conditions.

Examples 6 to 10

For examples 6 to 10, the composition of the O outlet stream was set with a 1 kg/hr mass flow rate and the O outlet stream comprised acetic acid, water, and carbon monoxide as illustrated in Table 2. Five different simulations were performed while varying the pressure of the WGS/H reactor and the pressure of the dehydration reactor from 100 kPag to 500 kPag in 100 kPag increments as illustrated in Table 2. The temperature of the WGS/H reactor and the dehydration reactor were each kept constant at 100° C.

TABLE 2

|  |  | O outlet stream | WGS/H Outlet Stream | | | | | Dehydration Outlet Stream | | | | |
|---|---|---|---|---|---|---|---|---|---|---|---|---|
|  |  | Ex. 6-10 | Ex. 6 | Ex. 7 | Ex. 8 | Ex. 9 | Ex. 10 | Ex. 6 | Ex. 7 | Ex. 8 | Ex. 9 | Ex. 10 |
|  | Pressure (kPag) | 100 | 100 | 200 | 300 | 400 | 500 | 100 | 200 | 300 | 400 | 500 |
|  | Volume Flow (L/min) | 19.48 | 17.58 | 8.5 | 5.56 | 4.11 | 3.24 | 19.40 | 9.28 | 5.99 | 4.39 | 3.44 |
| Mass | $CH_3OOH$ | 0.3 | 0.07 | 0.08 | 0.09 | 0.1 | 0.11 | 0.03 | 0.04 | 0.06 | 0.07 | 0.08 |
| Fraction | $H_2O$ | 0.4 | 0.28 | 0.29 | 0.29 | 0.29 | 0.29 | 0.34 | 0.34 | 0.33 | 0.33 | 0.32 |
|  | CO | 0.3 | 0 | 0 | 0 | 0 | 0 | 0 | 0 | 0 | 0 | 0 |
|  | $CO_2$ | 0 | 0.48 | 0.45 | 0.44 | 0.43 | 0.42 | 0.49 | 0.47 | 0.46 | 0.45 | 0.44 |
|  | $C_2H_5OH$ | 0 | 0.18 | 0.18 | 0.18 | 0.17 | 0.17 | 0.04 | 0.07 | 0.09 | 0.1 | 0.11 |
|  | $H_2$ | 0 | 0.01 | 0 | 0 | 0 | 0 | 0.1 | 0 | 0 | 0 | 0 |
|  | $C_2H_4$ | 0 | 0 | 0 | 0 | 0 | 0 | 0.1 | 0.08 | 0.06 | 0.05 | 0.05 |
|  | Heat of Reaction (KJ/mol) | 223.29 | 258.02 | 262.63 | 264.49 | 265.53 | 266.22 | 234.68 | 241.70 | 246.35 | 249.73 | 252.31 |

As shown in Table 2, the exothermic nature of the WGS reaction and hydrogenation reactions within the WGS/H reactor caused a substantial portion of the acetic acid, carbon monoxide, and water to be converted to ethanol, carbon dioxide, and hydrogen. Additionally, the dehydration reaction of the ethanol to ethylene in the dehydration reactor is favored at lower pressures for these conditions. The change in pressure caused insignificants changes in ethanol production.

Various aspects of the invention include, but are not limited to, the aspects listed in the following numbered clauses.

1. A method for converting a lower alkane to an alkene comprising:
   providing an input stream comprising oxygen and the lower alkane to an oxidative dehydrogenation (ODH) reactor;
   converting at least a portion of the lower alkane to the alkene in the ODH reactor and producing an ODH outlet stream comprising the alkene, an oxygenate, water, and carbon monoxide;
   removing at least a substantial portion of the alkene from the ODH outlet stream including producing an alkene outlet stream comprising the at least a substantial portion of the alkene, and an oxygenate outlet stream comprising at least a substantial portion of the oxygenate, at least a substantial portion of the water, and at least a portion of the carbon monoxide;
   providing the oxygenate outlet stream to a water gas shift/hydrogenation (WGS/H) reactor including a catalyst; and
   reacting the oxygenate outlet stream within the WGS/H reactor including generating hydrogen, in situ, from the carbon monoxide and water of the oxygenate outlet stream, converting at least a portion of the oxygenate and hydrogen to an alcohol, and producing an alcohol outlet stream comprising at least a substantial portion of the alcohol.
2. The method of clause 1, further comprising maintaining the WGS/H reactor at a temperature of 100° C. to 500° C.
3. The method of clause 1-2, further comprising maintaining the WGS/H reactor at a pressure of 100 kPag to 500 kPag.
4. The method of clause 1-3, wherein the oxygenate outlet stream has a temperature of 50° C. to 350° C.
5. The method of clause 1-4, wherein the catalyst is non-acidic.
6. The method of clause 1-5, wherein the catalyst comprises at least one of copper, iron, platinum, tin, and chromium.
7. The method of clause 1-6 wherein the ODH outlet stream further comprises at least one of an unreacted alkane, carbon dioxide, and oxygen.
8. The method of clause 1-7, wherein the oxygenate outlet stream comprises at least 5% water by weight.
9. The method of clause 1-8, wherein the oxygenate outlet stream comprises at least 30% water by weight.
10. The method of clause 1-9, wherein the oxygenate outlet stream comprises at least 10% carbon monoxide by weight.
11. The method of clause 1-10, wherein the oxygenate outlet stream comprises at least 10% oxygenate by weight.
12. The method of clause 1-11, wherein the oxygenate outlet stream is substantially free of hydrogen.
13. The method of clause 1-12, wherein the oxygenate comprises at least one of acetic acid, acrylic acid, maleic acid, and maleic anhydride.
14. The method of clause 1-13, wherein the alkane comprises ethane and the alkene comprises ethylene.
15. The method of clause 1-14, wherein the alcohol comprises ethanol.
16. The method of clause 1-15, further comprising:
providing the alcohol outlet stream to a dehydration reactor, and converting at least a portion of the alcohol in the alcohol outlet stream to a second alkene.
17. The method of clause 16, wherein the second alkene comprises ethylene.
18. The method of clause 1-17, further comprising producing olefin derivatives from the second alkene.
19. The method of clause 18, wherein the olefin derivatives comprise at least one of polyethylene, polypropylene, ethylene oxide, propylene oxide, polyethylene oxide, polypropylene oxide, thermoplastic elastomers, and thermoplastic olefins.
20. The method of clause 19, wherein the polyethylene comprise at least one of homopolymers of ethylene, copolymers of ethylene and α-olefins, high density polyethylene (HDPE), medium density polyethylene (MDPE), low density polyethylene (LDPE), linear low density polyethylene (LLDPE), and very low density polyethylene (VLDPE).
21. An apparatus for oxidative dehydrogenation (ODH) of a lower alkane to an alkene, the apparatus comprising:
   an ODH reactor comprising an ODH inlet and an ODH outlet, the ODH inlet suitable for transporting an ODH inlet stream comprising the lower alkane and oxygen into the ODH reactor, the ODH outlet suitable for transporting an ODH outlet stream comprising the alkene, an oxygenate, water, and carbon monoxide;
   a separator comprising a separator inlet, an alkene outlet, and an oxygenate outlet, the separator inlet in fluid communication with the ODH outlet to receive the ODH outlet stream, the alkene outlet suitable for transporting an alkene outlet stream comprising at least a substantial portion of the alkene, the oxygenate outlet suitable for transporting an oxygenate outlet stream comprising at least a substantial portion of the oxygenate, at least a substantial portion of the water, and at least a portion of the carbon monoxide; and a water gas shift/hydrogenation (WGS/H) reactor comprising an WGS/H inlet and a WGS/H outlet, the WGS/H inlet in fluid communication with the oxygenate outlet to receive the oxygenate outlet stream, the WGS/H reactor including a catalyst and suitable to generate, in situ, hydrogen from the carbon monoxide and water of the oxygenate outlet stream, and the WGS/H outlet suitable for transporting an alcohol outlet stream comprising an alcohol.

22. The apparatus of clause 21, wherein the WGS/H reactor is suitable to operate at a temperature of 100° C. to 500° C.

23. The apparatus of clause 21-22, wherein the WGS/H reactor is suitable to operate at a pressure of 100 kPag to 500 kPag.

24. The apparatus of clause 21-23, wherein the oxygenate outlet stream has a temperature of 50° C. to 350° C.

25. The apparatus of clause 21-24, wherein the catalyst is non-acidic.

26. The apparatus of clause 21-25, wherein the catalyst comprises at least one of copper, iron, platinum, tin, and chromium.

27. The apparatus of clause 21-26, wherein the ODH outlet stream further comprises at least one of an unreacted alkane, carbon dioxide, and oxygen.

28. The apparatus of clause 21-27, wherein the oxygenate outlet stream comprises at least 5% water by weight.

29. The apparatus of clause 21-28, wherein the oxygenate outlet stream comprises at least 30% water by weight.

30. The apparatus of clause 21-29, wherein the oxygenate outlet stream comprises at least 10% carbon monoxide by weight.

31. The apparatus of clause 21-30, wherein the oxygenate outlet stream comprises at least 10% oxygenate by weight.

32. The apparatus of clause 21-31, wherein the oxygenate outlet stream is substantially free of hydrogen.

33. The apparatus of clause 21-32, wherein the oxygenate comprises at least one of acetic acid, acrylic acid, maleic acid, and maleic anhydride.

34. The apparatus of clause 21-33, wherein the alkane comprises ethane and the alkene comprises ethylene.

35. The apparatus of clause 21-34, wherein the alcohol comprises ethanol.

36. The apparatus of clause 21-35, further comprising:
a dehydration reactor comprising a dehydration inlet and a dehydration outlet, the dehydration inlet in fluid communication with the WGS/H outlet to receive the alcohol outlet stream, and the dehydration outlet suitable for transporting a second alkene stream comprising a second alkene.

37. The apparatus of clause 36, wherein the second alkene comprises ethylene.

38. The apparatus of clause 21-37, further comprising a polymerization reactor suitable to make olefin derivatives from the second alkene.

39. The apparatus of clause 38, wherein the olefin derivatives comprise at least one of polyethylene, polypropylene, ethylene oxide, propylene oxide, polyethylene oxide, polypropylene oxide, thermoplastic elastomers, and thermoplastic olefins.

40. The apparatus of clause 39, wherein the polyethylene comprise at least one of homopolymers of ethylene, copolymers of ethylene and α-olefins, high density polyethylene (HDPE), medium density polyethylene (MDPE), low density polyethylene (LDPE), linear low density polyethylene (LLDPE), and very low density polyethylene (VLDPE).

41. A system for oxidative dehydrogenation (ODH) of a lower alkane to an alkene, the system comprising:
an ODH reactor configured to receive an input stream comprising oxygen and the lower alkane, the ODH reactor configured to produce an ODH outlet stream comprising an alkene, an oxygenate, and a carbon-based oxide;
a separator configured to receive the ODH outlet stream, and remove at least a substantial portion of the alkene from the ODH outlet stream, the separator configured to produce an alkene outlet stream comprising at least a substantial portion of the alkene and an oxygenate outlet stream comprising at least a substantial portion of the oxygenate, at least a substantial portion of the water, and at least a portion of the carbon monoxide; and
a water gas shift/hydrogenation (WGS/H) reactor configured to receive the oxygenate outlet stream, the WGS/H reactor including a catalyst and configured to generate, in situ, hydrogen from the carbon monoxide and water of the oxygenate outlet stream, and convert at least a portion of the oxygenate and hydrogen to an alcohol.

42. The system of clause 41, wherein the WGS/H reactor is configured to operate at a temperature of 100° C. to 500° C.

43. The system of clause 41-42, wherein the WGS/H reactor is configured to operate at a pressure of 100 kPag to 500 kPag.

44. The system of clause 41-43, wherein the oxygenate outlet stream has a temperature of 50° C. to 350° C.

45. The system of clause 41-44, wherein the catalyst is non-acidic.

46. The system of clause 41-45, wherein the catalyst comprises at least one of copper, iron, platinum, tin, and chromium.

47. The system of clause 41-46, wherein the ODH outlet stream further comprises at least one of an unreacted alkane, carbon dioxide, and oxygen.

48. The system of clause 41-47, wherein the oxygenate outlet stream comprises at least 5% water by weight.

49. The system of clause 41-48, wherein the oxygenate outlet stream comprises at least 30% water by weight.

50. The system of clause 41-49, wherein the oxygenate outlet stream comprises at least 10% carbon monoxide by weight.

51. The system of clause 41-50, wherein the oxygenate outlet stream comprises at least 10% oxygenate by weight.

52. The system of clause 41-51, wherein the oxygenate outlet stream is substantially free of hydrogen.

53. The system of clause 41-52, wherein the oxygenate comprises at least one of acetic acid, acrylic acid, maleic acid, and maleic anhydride.

54. The system of clause 41-53, wherein the alkane comprises ethane and the alkene comprises ethylene.

55. The system of clause 41-54, wherein the alcohol comprises ethanol.

56. The system of clause 41-55, further comprising:
a dehydration reactor configured to receive the alcohol outlet stream and convert at least a portion of the alcohol in the alcohol outlet stream to a second alkene.

57. The system of clause 56, wherein the second alkene comprises ethylene.

58. The system of clause 41-57, further comprising a polymerization reactor suitable to make olefin derivatives from the second alkene.

59. The system of clause 58, wherein the olefin derivatives comprise at least one of polyethylene, polypropylene, ethylene oxide, propylene oxide, polyethylene oxide, polypropylene oxide, thermoplastic elastomers, and thermoplastic olefins.

60. The system of clause 59, wherein the polyethylene comprise at least one of homopolymers of ethylene, copolymers of ethylene and α-olefins, high density polyethylene (HDPE), medium density polyethylene (MDPE), low density polyethylene (LDPE), linear low density polyethylene (LLDPE), and very low density polyethylene (VLDPE).

One skilled in the art will recognize that the herein described components, devices, operations/actions, and objects, and the discussion accompanying them are used as examples for the sake of conceptual clarity and that various configuration modifications are contemplated. Consequently, as used herein, the specific examples/embodiments set forth and the accompanying discussion are intended to be representative of their more general classes. In general, use of any specific exemplar is intended to be representative of its class, and the non-inclusion of specific components, devices, operations/actions, and objects should not be taken limiting.

While the present disclosure provides descriptions of various specific aspects for the purpose of illustrating various aspects of the present disclosure and/or its potential applications, it is understood that variations and modifications will occur to those skilled in the art. Accordingly, the invention or inventions described herein should be understood to be at least as broad as they are claimed, and not as more narrowly defined by particular illustrative aspects provided herein.

INDUSTRIAL APPLICABILITY

The process is applicable for the oxidative dehydrogenation (ODH) of lower alkanes into a corresponding alkene and associated by-products. The process is applicable to converting oxygenate ODH by-products into alcohols using a water gas shift reaction, and optionally converting resulting alcohols into the corresponding alkene.

The invention claimed is:

1. A method for converting a lower alkane to an alkene comprising:
   providing an input stream comprising oxygen and the lower alkane to an oxidative dehydrogenation (ODH) reactor;
   converting at least a portion of the lower alkane to the alkene in the ODH reactor and producing an ODH outlet stream comprising the alkene, an oxygenate, water, and carbon monoxide;
   providing at least a portion of the ODH outlet stream to a water gas shift/hydrogenation (WGS/H) reactor, the WGS/H reactor comprising a WGS/H catalyst;
   converting within the WGS/H reactor at least a portion of the carbon monoxide and at least a portion of the water to carbon dioxide and hydrogen; and
   converting within the WGS/H reactor at least a portion of the oxygenate and at least a portion of the hydrogen to an alcohol and producing an alcohol outlet stream comprising at least a substantial portion of the alcohol.

2. The method of claim 1, further comprising maintaining the WGS/H reactor at a temperature of 100° C. to 500° C.

3. The method of claim 1, further comprising maintaining the WGS/H reactor at a pressure of 100 kPag to 500 kPag.

4. The method of claim 1, wherein the ODH outlet stream is provided to the WGS/H reactor at a temperature of from 50° C. to 400° C.

5. The method of claim 1, further comprising providing the alcohol outlet stream to a dehydration reactor and converting at least a portion of the alcohol in the alcohol outlet stream to a second alkene.

6. The method of claim 5, wherein the second alkene comprises ethylene.

7. The method of claim 5, further comprising producing olefin derivatives from at least one of the alkene and the second alkene.

8. An apparatus for oxidative dehydrogenation (ODH) of a lower alkane to an alkene, the apparatus comprising:
   an ODH reactor comprising an ODH inlet and an ODH outlet, the ODH inlet suitable for transporting an ODH inlet stream comprising the lower alkane and oxygen into the ODH reactor, the ODH outlet suitable for transporting an ODH outlet stream comprising the alkene, an oxygenate, water, and carbon monoxide; and
   a water gas shift/hydrogenation (WGS/H) reactor comprising an WGS/H inlet and a WGS/H outlet, the WGS/H inlet in fluid communication with the ODH outlet to receive the ODH outlet stream, the WGS/H reactor including a WGS/H catalyst and suitable to generate, in situ, hydrogen and carbon dioxide from the carbon monoxide and water of the ODH outlet stream, and the WGS/H outlet suitable for transporting an alcohol outlet stream comprising an alcohol.

9. The apparatus of claim 8, wherein the WGS/H catalyst is non-acidic.

10. The apparatus of claim 8, wherein the WGS/H catalyst comprises at least one of copper, iron, platinum, tin, and chromium.

11. The apparatus of claim 8, wherein the ODH outlet stream further comprises at least one of an unreacted alkane, carbon dioxide, and oxygen.

12. The apparatus of claim 8, wherein the ODH outlet stream comprises at least 5% water by weight.

13. The apparatus of claim 8, wherein the ODH outlet stream comprises at least 30% water by weight.

14. The apparatus of claim 8, wherein the ODH outlet stream comprises at least 2% carbon monoxide by weight.

15. The apparatus of claim 8, wherein an oxygenate outlet stream separated from the ODH outlet stream comprises at least 5% oxygenate by weight.

16. The apparatus of claim 8, wherein the ODH outlet stream is substantially free of hydrogen.

17. The apparatus of claim 8, wherein the oxygenate comprises at least one of acetic acid, acrylic acid, maleic acid, and maleic anhydride.

18. The apparatus of claim 8, wherein the alkane comprises ethane and the alkene comprises ethylene.

19. The apparatus of claim 8, wherein the alcohol comprises ethanol.

20. The apparatus of claim 8, further comprising a dehydration reactor comprising a dehydration inlet and a dehydration outlet, the dehydration inlet in fluid communication with the WGS/H outlet to receive the alcohol outlet stream, and the dehydration outlet suitable for transporting a second alkene stream comprising a second alkene.

21. The apparatus of claim 20, wherein the second alkene comprises ethylene.

22. The apparatus of claim 20, further comprising a polymerization reactor suitable to make olefin derivatives from the alkene, the second alkene or both the alkene and the second alkene.

23. The apparatus of claim 22, wherein the olefin derivatives comprise at least one of polyethylene, polypropylene, ethylene oxide, propylene oxide, polyethylene oxide, polypropylene oxide, thermoplastic elastomers, and thermoplastic olefins.

24. The apparatus of claim 23, wherein the polyethylene comprise at least one of homopolymers of ethylene, copolymers of ethylene and α-olefins, high density polyethylene (HDPE), medium density polyethylene (MDPE), low density polyethylene (LDPE), linear low density polyethylene (LLDPE), and very low density polyethylene (VLDPE).

25. A system for oxidative dehydrogenation (ODH) of a lower alkane to an alkene, the system comprising:
an ODH reactor configured to receive an input stream comprising oxygen and the lower alkane, the ODH reactor configured to produce an ODH outlet stream comprising an alkene, an oxygenate, water and carbon monoxide; and
a water gas shift/hydrogenation (WGS/H) reactor configured to receive the ODH outlet stream, the WGS/H reactor including a WGS/H catalyst and configured to generate hydrogen and carbon dioxide from the carbon monoxide and water of the ODH outlet stream and convert at least a portion of the oxygenate and hydrogen to an alcohol.

26. The system of claim 25, wherein the oxygenate comprises at least one of acetic acid, acrylic acid, maleic acid, and maleic anhydride.

27. The system of claim 25, wherein the alkane comprises ethane and the alkene comprises ethylene.

28. The system of claim 25, wherein the alcohol comprises ethanol.

29. The system of claim 25, further comprising a dehydration reactor configured to receive the alcohol from the WGS/H reactor and convert at least a portion of the alcohol in the alcohol outlet stream to a second alkene.

30. The system of claim 29, wherein the second alkene comprises ethylene.

\* \* \* \* \*